US012748100B2

(12) United States Patent
(10) Patent No.: US 12,748,100 B2
(45) Date of Patent: *Sep. 29, 2026

Heeger et al.

(54) RAPID TESTING MECHANISM AND METHOD FOR RESPIRATORY VIRAL PATHOGENS

(71) Applicants: Brandon Heeger, Avon, IN (US); Ajay Lajmi, Pensacola, FL (US)

(72) Inventors: Brandon Heeger, Avon, IN (US); Ajay Lajmi, Pensacola, FL (US)

( * ) Notice: Subject to any disclaimer, the term of this patent is extended or adjusted under 35 U.S.C. 154(b) by 762 days.

This patent is subject to a terminal disclaimer.

(21) Appl. No.: 18/177,960

(22) Filed: Mar. 3, 2023

(65) Prior Publication Data

US 2023/0324366 A1 Oct. 12, 2023

Related U.S. Application Data

(63) Continuation of application No. 17/895,807, filed on Aug. 25, 2022, which is a continuation-in-part of (Continued)

(51) Int. Cl.
*G01N 33/497* (2006.01)
*C08L 1/00* (2006.01)
(Continued)

(52) U.S. Cl.
CPC .............. *G01N 33/497* (2013.01); *C08L 1/00* (2013.01); *C08L 5/10* (2013.01); *G01N 21/783* (2013.01);
(Continued)

(58) Field of Classification Search
CPC .. G01N 31/783; G01N 33/00; G01N 33/0027; G01N 33/48; G01N 33/483;
(Continued)

(56) References Cited

U.S. PATENT DOCUMENTS 4,806,313 A 2/1989 Ebersole
5,308,665 A 5/1994 Sadek
(Continued)

FOREIGN PATENT DOCUMENTS

CN 111264937 6/2020
CN 111264937 A * 6/2020 ......... A41D 13/1161
(Continued)

OTHER PUBLICATIONS

Machibe Translation of CN-111264937-A (Year: 2020).*
(Continued)

*Primary Examiner* — Nguyen Q. Ha
(74) *Attorney, Agent, or Firm* — Indiano Law Group LLC; E. Victor Indiano

(57) ABSTRACT

A rapid testing mechanism for respiratory viral pathogens includes a filter material positioned to capture exhaled breath particles from a respiratory tract. At least a portion of the filter material includes a pathogen binding adsorptive reagent, wherein the pathogen binding adsorptive reagent is a sulfated cellulose membrane. When the exhaled breath particles pass through the filter material, the following occur: when the binding adsorptive reagent reacts, a positive test for respiratory viral pathogens is indicated by the filter material; and when the pathogen binding adsorptive reagent does not react, a negative test for respiratory viral pathogens is individuated by the filter material.

6 Claims, 2 Drawing Sheets

Related U.S. Application Data application No. 17/500,126, filed on Oct. 13, 2021, now Pat. No. 11,454,625, which is a continuation of application No. 17/224,076, filed on Apr. 6, 2021, now Pat. No. 11,644,456.

(60) Provisional application No. 63/016,335, filed on Apr. 28, 2020.

(51) Int. Cl.

| | |
|---|---|
| ***C08L 5/10*** | (2006.01) |
| ***G01N 21/78*** | (2006.01) |
| ***G01N 33/00*** | (2006.01) |
| ***G01N 33/569*** | (2006.01) |
| ***G01N 35/00*** | (2006.01) |

(52) U.S. Cl.
CPC ... *G01N 33/0027* (2013.01); *G01N 33/56983* (2013.01); *G01N 35/00732* (2013.01); *G01N 33/4975* (2024.05); *G01N 2035/00752* (2013.01)

(58) Field of Classification Search
CPC ............. G01N 33/497; G01N 33/4975; G01N 33/569; G01N 33/56983; G01N 35/00732; G01N 2035/00752; C08L 1/00; C08L 5/10
See application file for complete search history.

(56) References Cited

U.S. PATENT DOCUMENTS

| | | | | |
|---|---|---|---|---|
| 6,062,220 | A | 5/2000 | Whitaker | |
| 7,052,854 | B2 | 5/2006 | Melker | |
| 11,103,668 | B2 | 8/2021 | Duveen | |
| 11,408,023 | B2 | 8/2022 | Young | |
| 2001/0019821 | A1 | 9/2001 | Smith | |
| 2008/0264259 | A1 | 10/2008 | Leung | |
| 2009/0255535 | A1 | 10/2009 | Kanzer | |
| 2013/0334042 | A1 * | 12/2013 | Grieve | C12Q 1/005 204/403.01 |
| 2017/0356899 | A1 | 12/2017 | Guder | |
| 2018/0242884 | A1 | 8/2018 | Kulkarni | |
| 2020/0323292 | A1 | 10/2020 | Chiang | |
| 2021/0086005 | A1 | 3/2021 | O'Brien | |
| 2021/0321903 | A1 | 10/2021 | Daniels | |
| 2021/0371905 | A1 | 12/2021 | Haselton | |
| 2022/0192537 | A1 | 6/2022 | Milner | |
| 2022/0339038 | A1 | 10/2022 | Greene | |
| 2023/0103369 | A1 * | 4/2023 | Gluckman | B01J 20/268 435/5 |

FOREIGN PATENT DOCUMENTS

| | | | | | |
|---|---|---|---|---|---|
| CN | 111505076 | A | * | 8/2020 | A41D 31/065 |
| CN | 111378018 | | | 1/2021 | |
| CN | 212483445 | | | 2/2021 | |
| CN | 212938027 | U | * | 4/2021 | A41D 13/11 |
| CN | 215455610 | U | * | 1/2022 | |
| GB | 2339904 | | | 2/2000 | |
| JP | 06180318 | | | 6/1994 | |
| TW | 590783 | | | 6/2004 | |
| WO | 9956128 | | | 11/1999 | |
| WO | 2021165448 | | | 8/2021 | |

OTHER PUBLICATIONS

Machine Translation of CN-111505076-A (Year: 2020).*
Machine Translation of CN-212938027-U (Year: 2020).*
Sulfate vs. Sulfonate (https://thisvsthat.io/sulfate-vs-sulfonate) (Year: 2025).*
Machine Translation of CN-215455610-U (Year: 2022).*
Mycroft-West et al, "The 2019 coronavirus (SARS-CoV-2) surface protein (Spike) S1 Receptor Binding Domain undergoes conformational change upon heparin binding", Mar. 2, 2020.
Fei Ke et al., "Ranavirusus Bind Cells from Different Species through Interaction with Heparan Sulfate", Virusus, Jun. 29, 2019.

* cited by examiner

RAPID TESTING MECHANISM AND METHOD FOR RESPIRATORY VIRAL PATHOGENS

CROSS-REFERENCE TO RELATED APPLICATIONS

This patent application is a continuation of U.S. patent application Ser. No. 17/895,807, filed on Aug. 25, 2022, which is a continuation-in-part of U.S. patent application Ser. No. 17/500,126, filed on Oct. 13, 2021 (which has issued as U.S. Pat. No. 11,454,625 on Sep. 27, 2022), which is a continuation of U.S. patent application Ser. No. 17/2424,076, filed on Apr. 6, 2021, and claims the benefit of U.S. Provisional Patent Application Ser. No. 63/016,335, filed on Apr. 8, 2020; all of which are incorporated herein by reference.

TECHNICAL FIELD

The present disclosure relates to the field of respiratory viral pathogen testing. More specifically, the present invention is directed to a rapid mechanism and method for respiratory viral pathogen testing.

BACKGROUND

Conventionally, viral testing is aimed to identify a specific virus. In most situations, identifying a specific virus allows for the collection of epidemiological data and the opportunity for targeted treatment. For example, a patient diagnosed with a viral infection due to influenza might be provided with a prescription of antiviral medication.

However, for the vast majority of respiratory viruses, identifying the specific virus provides little benefit, as the treatment, including supportive care, does not change. As such, testing causes unnecessary cost and burden on the healthcare system. Similarly, there is currently little to no utility in screening asymptomatic individuals, outside of a pandemic or other unique situation.

In the setting of a pandemic, such as when a novel virus is involved, there is typically a lapse in development, production, and distribution of novel viral detection agents. This time delay allows for viral spread without epidemiologic data. Further complicating the scenario are asymptomatic carriers, such as with the recent COVID-19 pandemic. Identifying asymptomatic carriers has proven to be a unique challenge, and the lack of identification of asymptomatic carriers undoubtedly contributes to disease spread. For example, a person who is admitted to the hospital, without clinical evidence of a respiratory virus, might in fact be carrying, and spreading, the COVID-19 virus.

Due to testing limitations, including availability, cost, resource utilization, and time delay until test result, these individuals entering the hospital are typically not screened. They might be admitted to the hospital and spread the disease, unbeknownst to them and the numerous hospital employees they encounter. A similar scenario occurs even when cursory screening is deployed. For example, in the beginning of the COVID-19 pandemic people were being screened for the virus by answering a screening questionnaire and testing for the presence of a fever. This screening is low yield, especially when considering asymptomatic carriers. Innumerable scenarios such as the above could be described.

The present technology is directed to and addresses the issues identified above.

SUMMARY

The present disclosure relates to a system and method for respiratory viral pathogen testing.

According to one aspect of the present disclosure, a rapid testing mechanism for respiratory viral pathogens includes a filter material positioned to capture exhaled breath particles from a respiratory tract. At least a portion of the filter material includes a pathogen binding adsorptive reagent, wherein the pathogen binding adsorptive reagent is a sulfated cellulose membrane. When the exhaled breath particles pass through the filter material, the following occur: when the binding adsorptive reagent reacts, a positive test for respiratory viral pathogens is indicated by the filter material; and when the pathogen binding adsorptive reagent does not react, a negative test for respiratory viral pathogens is individuated by the filter material.

According to another aspect of the present disclosure, a method of testing for respiratory viral pathogens includes providing at least a portion of a filter material with a pathogen binding adsorptive reagent, which is a sulfated cellulose membrane, and capturing exhaled breath particles from a respiratory tract with the filter material. A positive test for respiratory viral pathogens is indicated, by the filter material, when the pathogen binding adsorptive agent reacts. A negative test for respiratory viral pathogens is indicated, by the filter material, when the pathogen binding adsorptive reagent does not react.

According to another aspect of the present disclosure, a standalone detection device for respiratory viral pathogens includes a filter material supported by the standalone detection device. The standalone detection device is configured and positioned for detection of proximate exhaled breath particles from a respiratory tract of a mammal without physically contacting the mammal. At least a portion of the filter material includes a pathogen binding adsorptive reagent, wherein the pathogen binding adsorptive reagent is heparin sepharose or a sulfated cellulose membrane. When the exhaled breath particles pass through the filter material, the following occur: when the binding adsorptive reagent reacts, a positive test for respiratory viral pathogens is indicated by the filter material; and when the pathogen binding adsorptive reagent does not react, a negative test for respiratory viral pathogens is indicated by the filter material.

Yet another aspect of the present disclosure includes a standalone detection system for respiratory viral pathogens. A filter material is supported by the standalone detection system. The standalone detection system is configured and positioned for detection of proximate exhaled breath particles from a respiratory tract of a mammal without physically contacting the mammal. At least a portion of the filter material includes a pathogen binding adsorptive reagent, wherein the pathogen binding adsorptive reagent is heparin sepharose or a sulfated cellulose membrane. When the exhaled breath particles pass through the filter material, the following occur: when the binding adsorptive reagent reacts, a positive test for respiratory viral pathogens is indicated by the filter material using a first color; and when the pathogen binding adsorptive reagent does not react, a negative test for respiratory viral pathogens is indicated by the filter material using a second color. The standalone detection system also includes a photodetector positioned to detect the first color or the second color and transmit an indication of the positive test or the negative test based on the detected first color or second color.

Yet another aspect of the present disclosure includes a standalone detection system for respiratory viral pathogens. A filter material is supported by the standalone detection system. The standalone detection system is configured and positioned for detection of proximate exhaled breath particles from a respiratory tract of a mammal without physically contacting the mammal. At least a portion of the filter material includes a pathogen binding adsorptive reagent, wherein the pathogen binding adsorptive reagent is heparin sepharose or a sulfated cellulose membrane. When the exhaled breath particles pass through the filter material, the following occur: when the binding adsorptive reagent reacts, a positive test for respiratory viral pathogens is indicated by the filter material using a first barcode configuration; and when the pathogen binding adsorptive reagent does not react, a negative test for respiratory viral pathogens is indicated by the filter material using a second barcode configuration. The standalone detection system also includes an optical scanner positioned to detect the first barcode or the second barcode and transmit an indication of the positive test or the negative test based on the detected first barcode configuration or second barcode configuration.

BRIEF DESCRIPTION OF THE DRAWINGS

Like reference numbers and designations in the various drawings indicate like element.

DETAILED DESCRIPTION

Before the present methods, implementations, and systems are disclosed and described, it is to be understood that this invention is not limited to specific synthetic methods, specific components, implementation, or to particular compositions, and as such may, of course, vary. It is also to be understood that the terminology used herein is for the purpose of describing particular implementations only and is not intended to be limiting.

As used in the specification and the claims, the singular forms "a, "an" and "the" include plural references unless the context clearly dictates otherwise. Ranges may be expressed in ways including from "about" one particular value, and/or to "about" another particular value. When such a range is expressed, another implementation may include from the one particular value. Another implementation may include from the one particular value and/or the other particular value. Similarly, when values are expressed as approximations, for example by use of the antecedent "about," it will be understood that the particular value forms another implementation. It will be further understood that the description includes instances where said event or circumstance occurs and instances where it does not.

Figure 1:
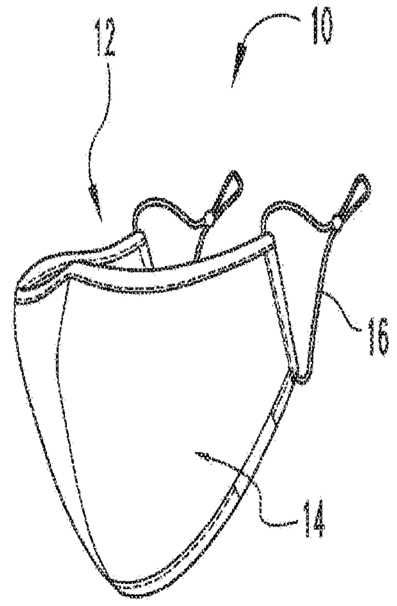
FIG. 1 depicts a simplified view of a view mask, according to an exemplary embodiment of the present disclosure.

The present disclosure relates generally to a rapid testing mechanism for respiratory viral pathogens. As shown in FIG. 1, an exemplary mechanism for facilitating the rapid testing may include a substrate housing structure 10, such as a face mask 12. The face mask 12, according to one embodiment, may comprise a material, such as filter material 14, straps/ear loops 16 to secure proper positioning of the face mask 12 on the face of a wearer, and a nose wire, which may also be used for positioning.

Typically, the filter material 14 is made up of multiple layers of material. For example, the filter material 14 may be a three-ply material including a ply of melt-blown polymer, such as polypropylene, polyethylene, or vinyl, positioned between two plies of non-woven fabric. Numerous factors, such as, for example, shape, size, thickness, number of layers, materials used, fit, breathability, filtering capabilities, disposability, etc. may all be considered, and may vary depending on the application. Additional layers may provide more filtration; however, different materials provide different filtering. Various alternatives to face masks 12 may also be used in combination with the teachings of the present disclosure.

The face mask 12, or an alternative, may be positioned to capture exhaled breath particles for a respiratory tract of a mammal. For example, the face mask 12 may be positioned to cover the mouth and nose of the mammal and capture breath particles in one or more layers of the filter material 14. According to an exemplary embodiment, a layer closest to the source of the exhaled breath particles may be a filter layer. Some household items may work as a filter layer in a homemade mask, including, for example, paper products that you can breathe through, such as coffee filters, paper towels, and toilet paper. As described above, various structures, materials and configurations may be incorporated into the present disclosure.

Knowing the average size of a virus is about 20-400 nanometers (0.02-0.04 microns), the filter material 14 may capture particles greater than about 400 nanometers (0.4 micrometers). This may allow viruses or viral particles to pass through the filter material 14. For example, the novel coronavirus is approximately 0.12 micrometers, so the novel coronavirus would pass freely through the filter material 14, but a bacteria that is 0.2 micrometers would be stopped by the filter 14. However, most viral particles do not travel independently, but are carried by larger media, such as water droplets, that would be stopped by the filter material 14. This filtering method is provided for exemplary purposes only and other filtering methods may be use. Further, one or more of the filtering methods may be implemented to narrow the viral pathogens that are detected.

At least a portion of the filter material 14 and/or another layer and/or another material is impregnated with or includes a pathogen binding adsorptive reagent. According to exemplary embodiments, the pathogen binding adsorptive reagent may be heparin Sepharose or sulfated cellulose, which may have a pore size of >0.4 micron. Although the amounts of the reagent may vary, according to an exemplary embodiment wherein the reagent is a liquid, the filter material 14 may be impregnated with 0.3 mL of the pathogen binding adsorptive reagent.

According to some embodiments, the filter material 14 is formed by using heparin-based porous adsorptive beads impregnated with liquid pathogen binding adsorptive reagent, then are combined with glycerin to slow the drying and extend viability of the binding adsorptive reagent. Further the filter material 14 may be packaged in a porous polymeric membrane.

Figure 2:
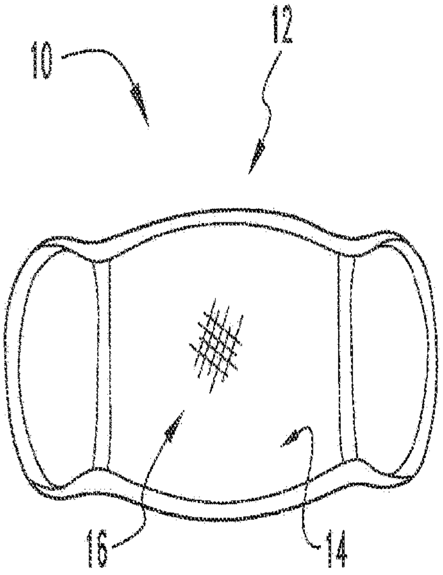
FIG. 2 depicts a simplified view of another face mask, indicating a positive test for respiratory viral pathogens.

When the face mask 12 is analyzed, if the binding adsorptive reagent reacts, a positive test for the respiratory viral pathogens is indicated by the filter material 14, as shown at 16 in FIG. 2. According to the exemplary embodiment, the indicator may be a particular color for a positive test. However, various different indicators may be used.

Figure 3:
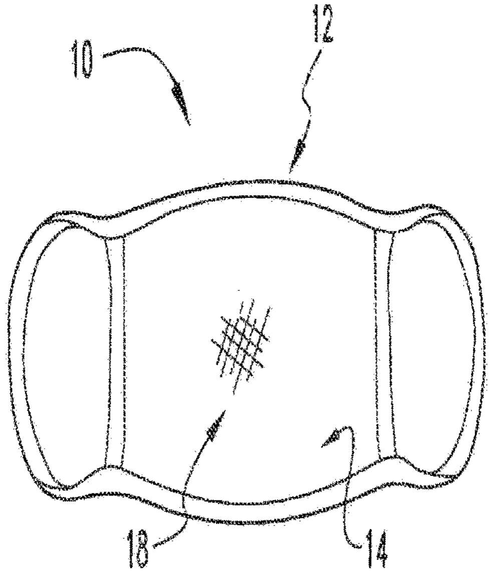
FIG. 3 depicts a simplified view of another face mask, indicating a negative test for respiratory viral pathogens.

If the pathogen binding reagent does not react, a negative test for respiratory viral pathogens is indicated by the filter material 14, as shown in FIG. 3. For example, a color different from the color indicating a positive test, may be used to indicate a negative test. In some cases, a negative test will be indicated when no change is detected.

In addition to the filtering, the disclosure utilizes affinity chromatography to signify the presence of a virus or viral particles, regardless of the speciation. Non-viral material that is less than 400 nanometer may pass through the filter material 14 but will not react with the reagent. This is a low cost, highly sensitive, and qualitative test that is not labor intensive, not prone to operator variation (i.e., correct placement of nasopharyngeal swabs), or reliant on expensive, advanced technology. This technology could be available for home or commercial testing or healthcare point of care testing. The design would allow it to be deployed in resource poor countries. This test may have other novel implications, such as screening mammals (humans or animals) for the presence of contagious diseases before boarding aircraft, within closed spaces, or other places where there might be an increased risk of disease transmission, irrespective of a pandemic state. As stated above, the filter material 14 is not restricted to use with a face mask. For example, the filter material 14 may be positioned within an aircraft, classroom, office etc. to detect a presence of the virus.

Figure 4:
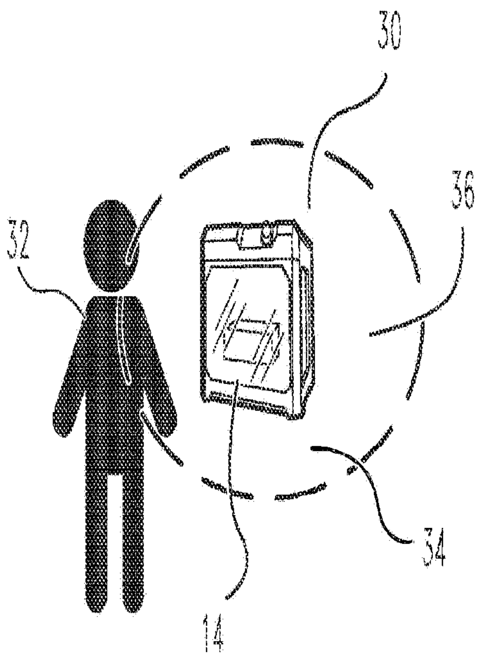
FIG. 4 depicts a simplified view of a standalone detection device for respiratory viral pathogens.

FIG. 4 depicts a simplified view of a standalone detection device 30 for respiratory viral pathogens. The standalone detection device 30 may be configured and positioned for detection of proximate exhaled breath particles from the respiratory tract of a mammal 32 without physically contacting the mammal 32. That is, the standalone detection device 30 may be capable of detecting respiratory viral pathogens within a proximity 34 of the standalone detection device 30, but is not in contact with the mammal 32, as is the case with the face mask 12.

The standalone detection device 30 may include a housing 36 or other component for supporting the filter material 14 described above. The standalone detection device 30 embodiment may be useful in environments such as, offices, planes, classrooms, etc., which may be somewhat contained environments.

A positive test may indicate the presence of a virus in the atmosphere and possible exposure. This will help mitigate spread, especially as people return without masks to school, office, etc.

The filter material 14 of the present embodiment may include the same capabilities as those described above with respect to the face mask 12, and may include, as a pathogen binding adsorptive reagent, heparin sepharose or a sulfated cellulose membrane.

Figure 5:
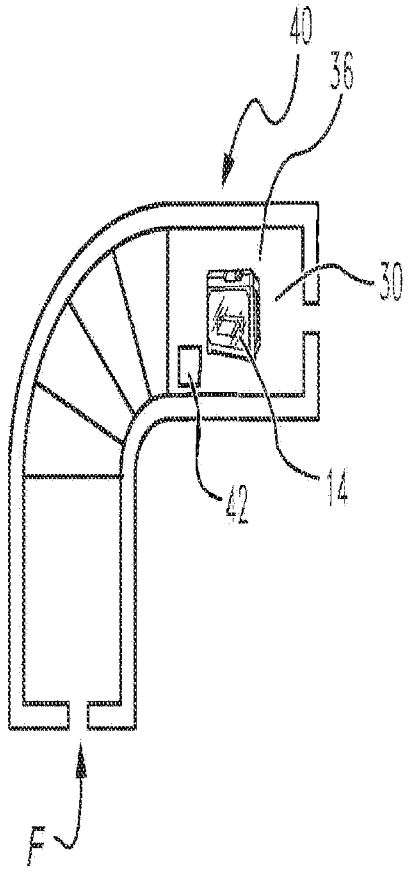
FIG. 5 depicts a simplified view of a standalone detection system for respiratory viral pathogens.

FIG. 5 depicts a simplified view of a standalone detection system 40 for respiratory viral pathogens. The standalone detection system 40 may or may not include the housing 36, but may include the filter material 14, as described above.

The standalone detection system 40 may also include a detection device 42, which may be, for example, a photodetector positioned to detect the first color or the second color, or other similar indicators, and transmit an indication of the positive test or the negative test based on the detected first color or second color. The photodetector (42) may, wirelessly or otherwise, transmit the test indication, especially a positive test indication, for conveyance and display of the test indication.

According to another exemplary embodiment, the detection device 42 may be an optical scanner. Rather than colors indicating a positive test or a negative test, barcodes having different configurations, may be used to indicate a positive or negative test. The optical scanner (42) may be positioned to detect a first barcode configuration, indicating a positive test, or a second barcode configuration, indicating a negative test, and transmit an indication of the positive test or the negative test based on the first barcode configuration or the second barcode configuration. The barcodes may be dynamic, in that the lines or patterns can change based on reaction of the pathogen binding adsorptive reagent.

An environment for utilizing the standalone detection system 40 may include, for example, an HVAC or air purification system, which may be a location or position that is not easily visible. As such, the detection device 42 may read and signify the positive test or negative test. In the HVAC or air purification system environment, the filter material 14 may be positioned upstream and/or downstream of an air intake or other area of greater airflow F which may force viral particles onto the binding substrate. In some cases, the filter material 14 may be positioned upstream and/or downstream of the air intake to test the efficacy of the filter material 14.

The present disclosure provides a quick and accurate means for detecting viruses that are aerosolized or expelled from the respiratory tract during breathing, coughing, or sneezing. The disclosure exploits commonalities in the composition of viruses expelled from the respiratory tract of a mammal.

Benefits of the disclosure also include the provision of a rapid qualitative assessment for respiratory viral pathogens, which disregards speciation in the immediacy. Using this highly sensitive, rapid, and qualitative assessment for respiratory viral pathogens, regardless of speciation, could assist in implementing proper triage, proper precautions could be taken, and more specific testing could be imposed, if indicated.

Particular embodiments of the subject matter have been described. Other embodiments are within the scope of the following claims.

The invention claimed is:

1. A standalone detection device for respiratory viral pathogens, including:

a filter material supported in a portable housing of the standalone detection device;

wherein the standalone detection device is configured and positioned for detection of proximate exhaled breath particles from a respiratory tract of a mammal without physically contacting the mammal;

wherein at least a portion of the filter material includes a pathogen binding adsorptive reagent, wherein the pathogen binding adsorptive reagent is heparin sepharose;

wherein, when the exhaled breath particles pass through the filter material, the following occurs:

when the binding adsorptive reagent reacts, a positive test for respiratory viral pathogens is indicated by the filter material; and when the pathogen binding adsorptive reagent does not react, a negative test for respiratory viral pathogens is indicated by the filter material.

2. The standalone detection device of claim 1, wherein the filter material includes multiple layers.

3. The standalone detection device of claim 1, wherein the filter material is packaged in a porous membrane.

4. The standalone detection device of claim 3, wherein the filter material includes multiple layers.

5. A standalone detection device for respiratory viral pathogens, including:

a filter material supported in a portable housing of the standalone detection device;

wherein the standalone detection device is configured and positioned for detection of proximate exhaled breath particles from a respiratory tract of a mammal without physically contacting the mammal;

wherein at least a portion of the filter material includes a pathogen binding adsorptive reagent, wherein the pathogen binding adsorptive reagent is heparin sepharose;

wherein, when the exhaled breath particles pass through the filter material, the following occurs:

when the binding adsorptive reagent reacts, a positive test for respiratory viral pathogens is indicated by the filter material; and when the pathogen binding adsorptive reagent does not react, a negative test for respiratory viral pathogens is indicated by the filter material;

wherein filter material includes porous adsorptive beads containing the pathogen binding adsorptive reagent.

6. The standalone detection device of claim 5, wherein the porous adsorptive beads containing the pathogen binding adsorptive reagent are positioned between two layers of multiple layers of the filter material.

* * * * *